US008449537B2

(12) United States Patent
Cao et al.

(10) Patent No.: US 8,449,537 B2
(45) Date of Patent: May 28, 2013

(54) ABLATION CATHETER WITH THERMALLY MEDIATED CATHETER BODY FOR MITIGATING BLOOD COAGULATION AND CREATING LARGER LESION

(75) Inventors: Hong Cao, Savage, MN (US); Xiaoping Guo, Eden Prairie, MN (US); Isaac Shai, Springfield, NJ (US); Michael Yang, Thousand Oaks, CA (US); Kedar Ravindra Belhe, Minnetonka, MN (US); Saurav Paul, Minnetonka, MN (US); Chou Thao, Brooklyn Park, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1366 days.

(21) Appl. No.: 11/618,692

(22) Filed: Dec. 29, 2006

(65) Prior Publication Data

US 2008/0161791 A1 Jul. 3, 2008

(51) Int. Cl.
*A61B 18/18* (2006.01)
(52) U.S. Cl.
USPC ............................................. 606/41; 606/32
(58) Field of Classification Search
USPC ........ 606/23–31, 41, 42, 45, 49; 607/96–102, 607/122
See application file for complete search history.

(56) References Cited

U.S. PATENT DOCUMENTS

| 5,257,635 | A | * | 11/1993 | Langberg | 607/122 |
|---|---|---|---|---|---|
| 5,545,161 | A | * | 8/1996 | Imran | 606/41 |
| 5,647,871 | A | * | 7/1997 | Levine et al. | 606/45 |
| 5,967,976 | A | * | 10/1999 | Larsen et al. | 600/374 |
| 6,287,305 | B1 | * | 9/2001 | Heim et al. | 606/41 |
| 6,461,351 | B1 | * | 10/2002 | Woodruff et al. | 606/32 |
| 2004/0116793 | A1 | * | 6/2004 | Taimisto et al. | 600/374 |
| 2006/0217701 | A1 | * | 9/2006 | Young et al. | 606/41 |

* cited by examiner

*Primary Examiner* — Linda Dvorak
*Assistant Examiner* — Amanda Scott
(74) *Attorney, Agent, or Firm* — Marsh Fischmann & Breyfogle LLP

(57) ABSTRACT

An ablation catheter is provided for ablating internal tissue of a patient. The catheter includes a distal end that is adapted to be inserted into a body cavity relative to a desired location therein (e.g., within the heart). An ablation electrode is connected relative to the distal end of the catheter for providing ablation energy to patient tissue. A heat sink is provided that is in thermal contact with the ablation electrode. The heat sink, in addition to being in thermal contact with the ablation electrode, is electrically isolated from the ablation electrode. This allows the heat sink to conduct heat away from the ablation electrode without dissipating electrical energy from the electrode. In this regard, the heat sink may prevent buildup of excess heat within the electrode that may result in blood coagulation and/or tissue charring.

16 Claims, 15 Drawing Sheets

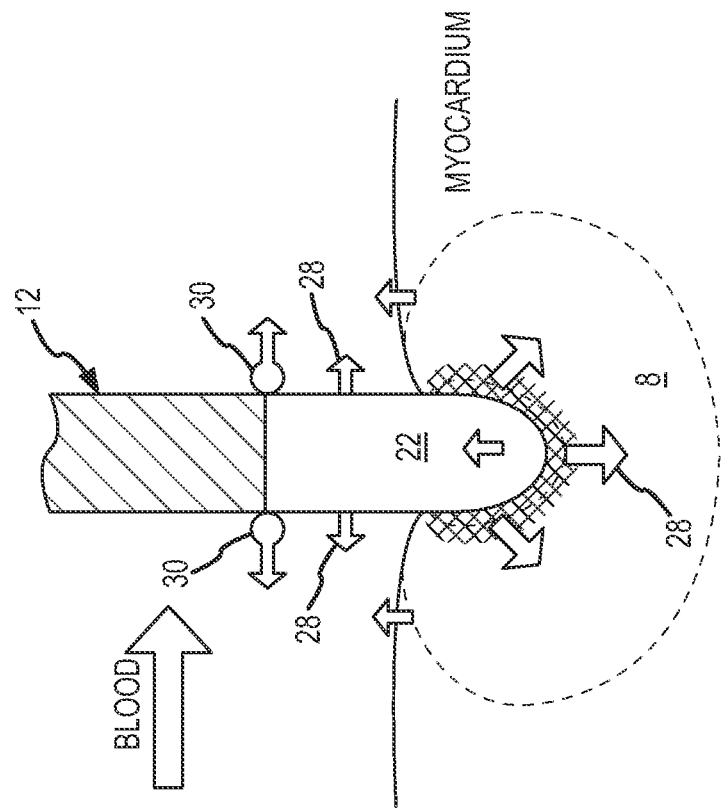
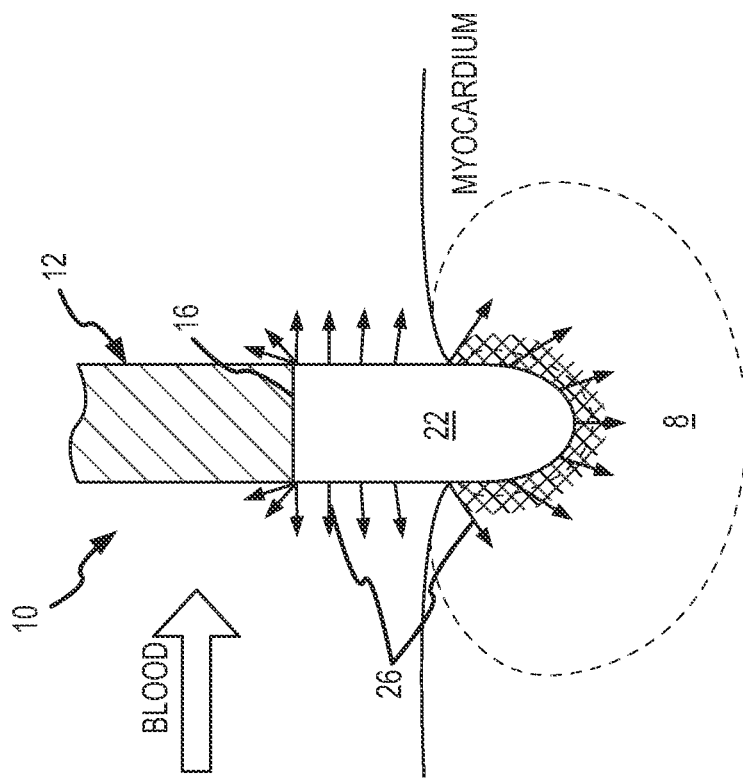

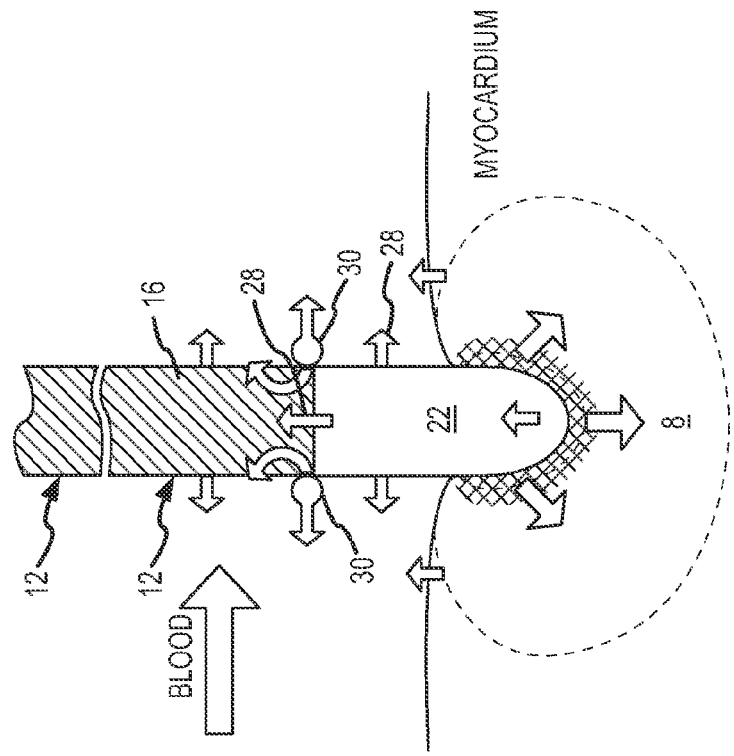
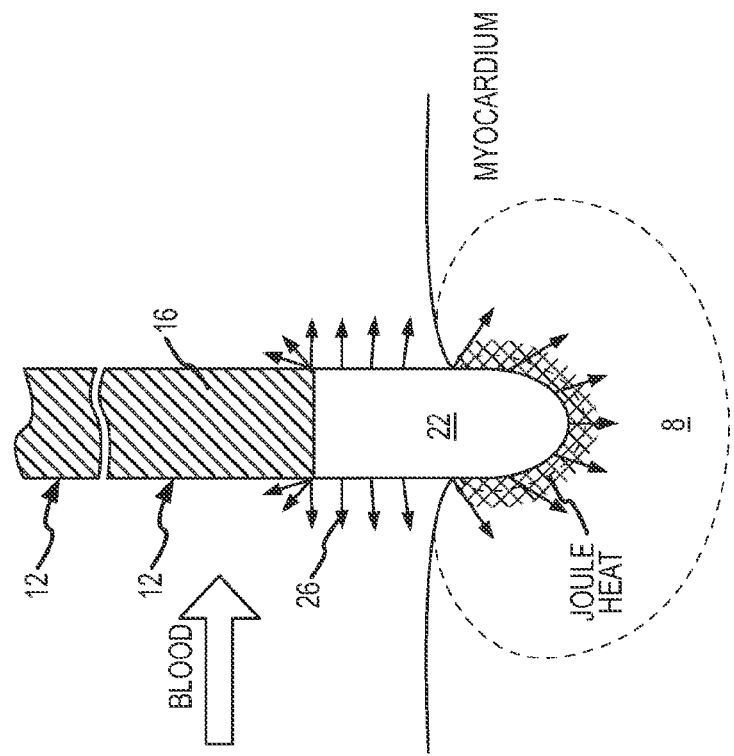

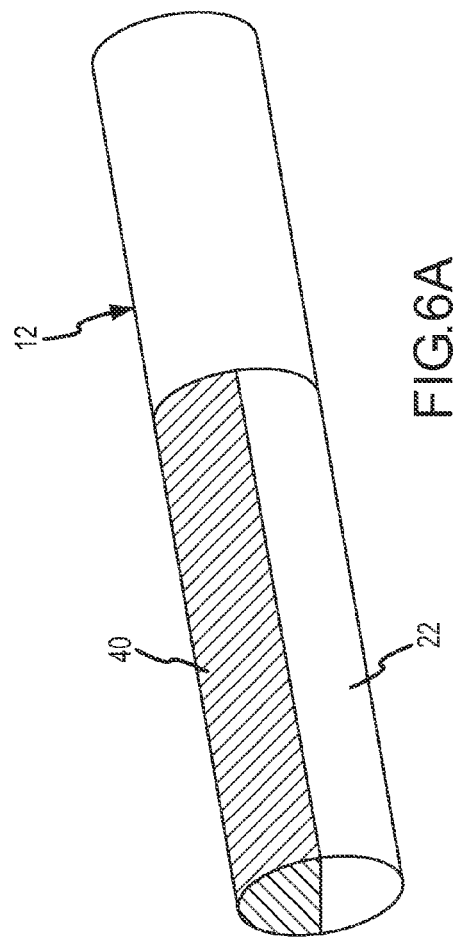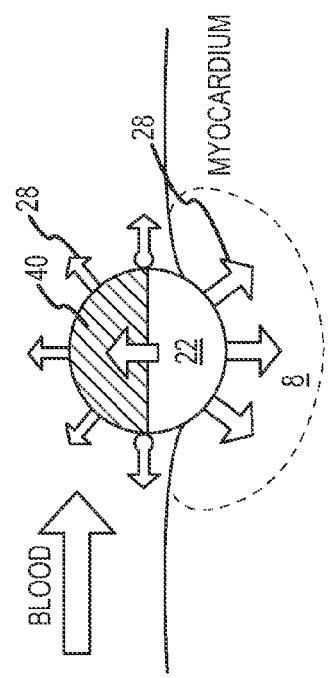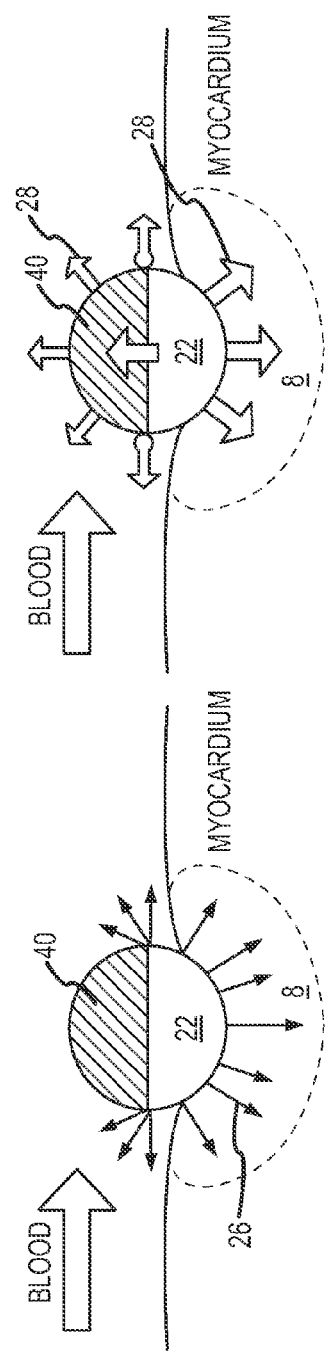

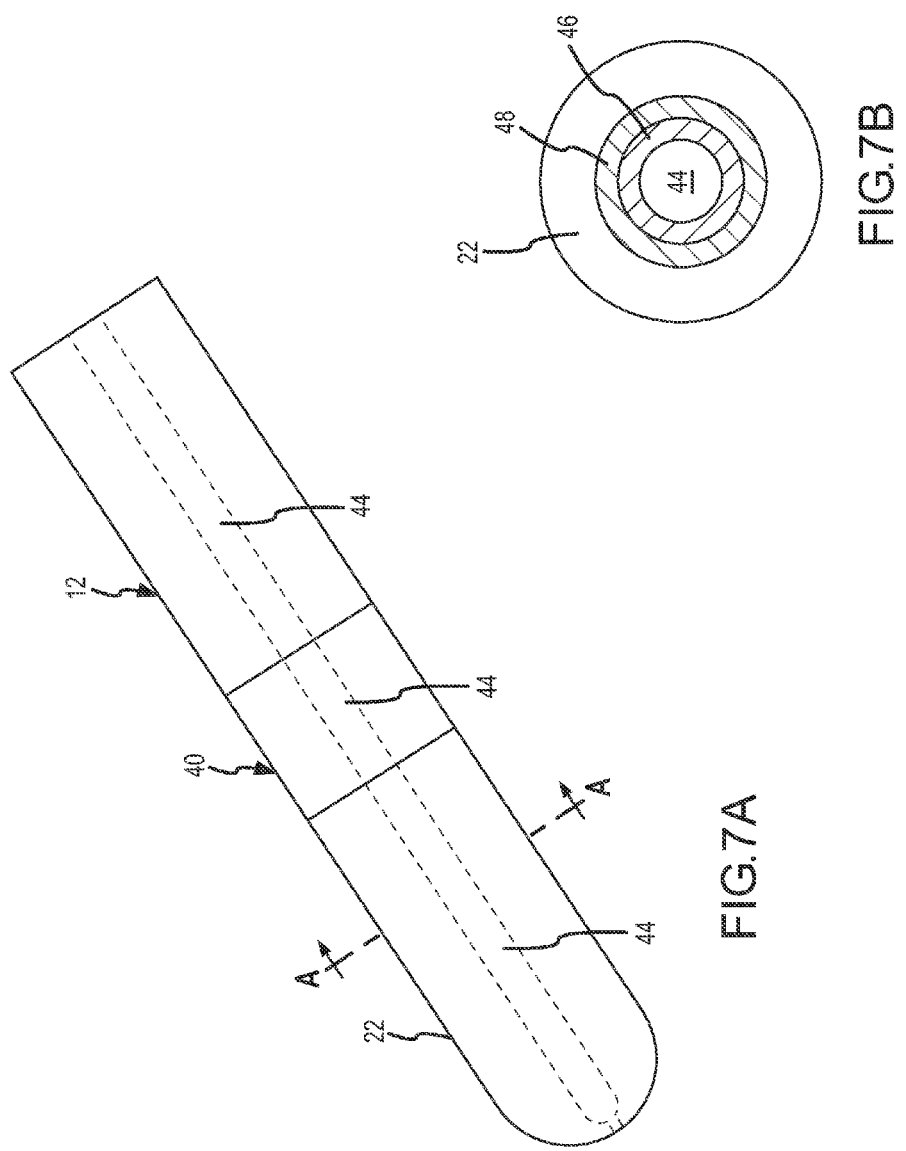

|  | PLASTIC | THERMAL POLYMER | ALUMINUM NITRIDE |
|---|---|---|---|
| MAXIMUM T | 95°C | 84°C | 74°C |
| ELECTRODE T | 85°C | 70°C | 56°C |
| LESION DEPTH | 5.2mm | 5.0mm | 4.9mm |

FIG.13

ABLATION CATHETER WITH THERMALLY MEDIATED CATHETER BODY FOR MITIGATING BLOOD COAGULATION AND CREATING LARGER LESION

BACKGROUND OF THE INVENTION a. Field of the Invention

The invention generally relates to catheters for the ablation of human tissue. One use of such catheters is for ablation of cardiac tissue. More specifically, the invention relates to an ablation catheter including a body having an electrode at a distal end for ablating tissue, as well as a thermally conductive heat sink that conducts heat away from the electrode and surrounding blood to reduce or prevent coagulation of the blood and/or tissue charring.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel near the surface of the body and is guided to a specific location within the body for examination, diagnosis, and treatment. For example, catheters can be used to convey an electrical stimulus to a selected location within the human body, e.g., for tissue ablation. In addition, catheters with sensing electrodes can be used to monitor various forms of electrical activity in the human body, e.g., for electrical mapping.

Catheters are used increasingly for medical procedures involving the human heart. Typically, the catheter is inserted in an artery or vein in the leg, neck, or arm of the patient and threaded, sometimes with the aid of a guide wire or introducer, through the vessels until a distal tip of the catheter reaches the desired location for the medical procedure in the heart. In the normal heart, contraction and relaxation of the heart muscle (myocardium) takes place in an organized fashion as electro-chemical signals pass sequentially through the myocardium from the sinoatrial (SA) node, which comprises a bundle of unique cells disposed in the wall of the right atrium, to the atrioventricular (AV) node and then along a well-defined route into the left and right ventricles.

Sometimes abnormal rhythms occur in the heart, which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal conduction system. These pathways are usually located in the fibrous tissue that connects the atrium and the ventricle.

Other abnormal arrhythmias sometimes occur in the atria, which are referred to as atrial arrhythmia. Three of the most common atrial arrhythmia are ectopic atrial tachycardia, atrial fibrillation, and atrial flutter. Atrial fibrillation can result in significant patient discomfort and even death because of a number of associated problems, including the following: an irregular heart rate, which causes patient discomfort and anxiety; loss of synchronous atrioventricular contractions, which compromises cardiac hemodynamics, resulting in varying levels of congestive heart failure; and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems, and other difficulties.

An increasingly common medical procedure for the treatment of certain types of cardiac arrhythmia is catheter ablation. During conventional catheter ablation procedures, an energy source is placed in contact with cardiac tissue to heat the tissue and create a permanent scar or lesion that is electrically inactive or noncontractile. During one procedure, the lesions are designed to interrupt existing conduction pathways commonly associated with arrhythmias within the heart. The particular area for ablation depends on the type of underlying arrhythmia.

Ablation of a specific location within the heart requires the precise placement of the ablation catheter within the heart. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy (placement of the catheter in relation to known features of the heart, which are marked by radiopaque diagnostic catheters that are placed in or at known anatomical structures, such as the coronary sinus, high right atrium, and the right ventricle).

The ablation catheter produces lesions and electrically isolate or render the tissue non-contractile at particular points in the cardiac tissue by physical contact of the cardiac tissue with an electrode of the ablation catheter and application of energy. The lesion partially or completely blocks the stray electrical signals to lessen or eliminate arrhythmia.

The energy necessary to ablate cardiac tissue and create a permanent lesion can be provided from a number of different sources. Originally, direct current was utilized although laser, microwave, ultrasound, and other forms of energy have also been utilized to perform ablation procedures. Because of problems associated with the use of DC current, however, radiofrequency (RF) has become the preferred source of energy for ablation procedures.

In addition to radiofrequency ablation catheters, thermal ablation catheters have been utilized. During thermal ablation procedures, a heating element, secured to the distal end of a catheter, heats thermally conductive fluid, which fluid then contacts the human tissue to raise its temperature for a sufficient period of time to ablate the tissue.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes. To form linear lesions within the heart using a conventional ablation tip electrode requires the utilization of procedures such as a "drag burn." The term "linear lesion" as used herein means an elongate, continuous lesion, whether straight or curved, that blocks electrical conduction. During a "drag burn" procedure, while ablating energy is supplied to the tip electrode, the tip electrode is drawn across the tissue to be ablated, producing a line of ablation. Alternatively, a series of points of ablation are formed in a line created by moving the tip electrode incremental distances across the cardiac tissue.

The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure, and other variables associated with a beating heart, especially an erratically beating heart. Unless an uninterrupted track of cardiac tissue is ablated, unablated tissue or incompletely ablated tissue may remain electrically active, permitting the continuation of the stray circuit that causes the arrhythmia. Generally, it has been discovered that more efficient ablation may be achieved if a linear lesion of cardiac tissue is formed during a single ablation procedure.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode, which often results in the formation of coagulum on the electrode, which reduces the efficiency of the ablation electrode. Accordingly, it is desirable to maintain the temperature of the electrode at a temperature that does not result in the coagulation of surrounding blood. However, it will be appreciated that this desire is balanced with the need to provide enough energy to create a lesion (e.g., ablate tissue) of a desired depth.

The temperature of an electrode may vary over its length and is dependent upon the duration that energy is applied to the electrode. For instance, the distal tip of the electrode, which may be contact with patient tissue, typically does not cause significant coagulation problems for short duration (e.g., single location) ablation procedures. That is, for short procedures conductive transfer of energy from the tip of the electrode may keep the electrode tip below coagulation temperatures. In contrast, proximal portions of the electrode, which are typically in contact with patient fluid (e.g., blood), depend upon convection to remove heat generated within the electrode and are apt to see significant temperature increases even during short ablation procedures. That is, the convective heat transfer with the surrounding blood alone may not be efficient enough to maintain the proximal portions of the electrode at a temperature that is below the coagulation temperature of blood. Further, for longer duration procedures or multiple single location procedures, heat may build-up throughout the electrode, which may result in coagulation for the entire electrode as well as the possibility of tissue charring.

One approach to lower catheter temperature and thereby reduce blood coagulation is to use ablation electrodes having an increased size. Such large electrodes (e.g., 8 mm or 10 mm electrodes) provide an increase surface area for convective heat transfer, which works to reduce electrode temperature. However, such large electrodes also reduce delivered energy density and therefore require increased ablation energy to create a desired lesion as energy is dissipated through the increased surface area to surrounding fluid.

To achieve efficient and effective ablation, coagulation of blood that is commonly associated with conventional ablation catheters should be avoided. This coagulation problem can be especially significant when linear ablation lesions or tracks are produced because such linear ablation procedures conventionally take more time than ablation procedures ablating only a single location and can result in heat build up within the electrode.

BRIEF SUMMARY OF THE INVENTION

It is desirable to prevent excessive heat build up within an electrode without necessarily having to increase the size of the electrode, which can lead to increased energy dissipation. In this regard, the inventors have recognized that it is desirable to increase the surface area of an electrode for convective cooling. However, the inventors have also recognized that an increase in the convective cooling surface area of an electrode need not increase the electrically conductive surface area of the electrode and therefore increase the energy dissipated by the electrode. That is, the inventors have recognized that use of a thermally conductive and electrically isolative heat sink that is in thermal contact with the electrode may provide improved cooling for the electrode without significantly altering the operating parameters of the electrode.

According to one aspect, an ablation catheter is provided for ablating internal tissue of a patient. The catheter includes a body having a proximal portion and a distal end. The distal end is adapted to be inserted into a body cavity relative to a desired location therein (e.g., within the heart). An ablation electrode is connected relative to the distal end of the catheter for providing ablation energy to patient tissue. A heat sink is in thermal contact with the ablation electrode. The heat sink, although in thermal contact with the ablation electrode, is electrically insulated (e.g., substantially electrically isolated) from the ablation electrode. This allows the heat sink to conduct heat away from the ablation electrode without dissipating electrical energy from the electrode. In this regard, the heat sink may prevent build-up of excess heat within the electrode that may result in blood coagulation and/or tissue charring.

Generally, the heat sink is formed of a thermally conductive and electrically resistive element that may be in direct physical contact with the ablation electrode. Alternatively, the heat sink and electrode may be interconnected by an intermediate member, such as, for example, a thermally conductive adhesive. To provide desired conductive heat transfer from the ablation electrode, the heat sink may have a thermal conductivity in excess of about 0.01 watts/cm Kelvin. In a further embodiment, the heat sink may have a thermal conductivity of greater than about 0.1 watts/cm Kelvin. In a yet further embodiment, the heat sink may have a thermal conductivity of greater than 1.0 watts/cm Kelvin. In order to be electrically insulated from the ablation electrode, the heat sink may have an electrical resistivity that prevents most or all electrical conduction therein. In this regard, the heat sink may have an electrical resistivity in excess of that of the ablation electrode and/or patient tissue. In another arrangement, the electrical resistivity is greater than about $1.0 \times 10^3$ ohm cm. In this regard, the heat sink may be any material that exhibits high electrical resistivity in conjunction with desired thermal conductivity.

Some non-limiting examples of materials that may be utilized as a heat sink with the catheter include diamond, diamond-like carbon, aluminum nitride, boron nitride, thermoconductive epoxies and thermal polymers (i.e., thermoconductive polymers). Such polymers may include conductive media within their structure. In the latter regard, use of a thermoconductive polymer may allow the distal end of the catheter body to form the heat sink. That is, the catheter body may be formed of a polymer/plastic having enhanced thermal conductivity properties.

In other arrangements, the heat sink may be separately formed from the ablation electrode and/or the distal end of the catheter body. In such arrangements, the heat sink may be attached to the ablation electrode and/or the catheter body in any appropriate manner. In one arrangement, the heat sink is disposed between the ablation electrode and the distal end of the catheter body. In such an arrangement, the heat sink may include one or more internal passageways or lumens that permit internal access between the ablation electrode and the distal end of the catheter body. Such internal passageways may be aligned with lumens in the catheter body and/or ablation electrode such that, for example, fluid may be provided from the catheter body, through the heat sink and through the electrode. Additionally, electrical wiring and/or guide wires may extend from the catheter body, through the heat sink and to the electrode. Where the electrode, heat sink and catheter body are disposed in a series, outside surfaces of these components may be conformal or otherwise share a common cross-sectional shape.

In another arrangement, the heat sink may be attached to the electrode over a portion or all of its length. In such an arrangement, the electrode may have a distal tip and a proximal end (e.g., for attachment to the catheter body), and the heat sink may be attached to a portion of the length of the electrode. In another arrangement, the heat sink may extend over essentially the entire length of one surface of the electrode.

In another aspect, an ablation electrode is provided that has a portion of the active surface of the electrode covered by an electrically insulative material. This electrically insulative material or electrical insulator prevents dissipation of energy from the electrode to surrounding media (e.g., tissue and/or fluid). In such an arrangement, the size of the electrode may be increased to provide additional convective cooling. The electric insulator may prevent the dissipation of energy from a portion of the outside surface of the electrode and thereby reduce the energy required by the electrode for an ablation procedure. Likewise, additional energy may be available for an ablation procedure.

In one arrangement, the electrically insulative material is applied to an outside surface of the electrode. Such material may be applied as, for example, a film or wrap (e.g., tape) that may extend over or around a portion of the electrode that is not intended to contact patient tissue. Such an electrically insulative material may be thin enough to permit thermal conductivity from the electrode to surrounding media to maintain a desired temperature within the electrode. In another arrangement, the electrically insulative material may also be thermally conductive to enhance heat transfer from the electrode to surrounding material. In one arrangement, a heat shrink tape may be applied to a proximal portion of an electrode while the distal tip of the electrode remains uncovered such that it may be utilized to apply ablation energy to tissue.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 2A and 2B illustrate energy dissipation and thermal conductivity, respectively, in one embodiment of an ablation electrode.

FIGS. 5A and 5B illustrate energy dissipation and thermal conductivity, respectively, in a third embodiment of an ablation electrode in accordance with the present disclosure.

FIG. 6A illustrates a perspective view of a fourth embodiment of an ablation electrode in accordance with the present disclosure.

FIGS. 6B and 6C illustrate energy dissipation and thermal conductivity, respectively, of the ablation electrode of FIG. 6A FIGS. 7A and 7B illustrate perspective and cross-sectional views, respectively, of a fifth embodiment of an ablation electrode in accordance with the present disclosure.

FIG. 13 is a table of the temperature distributions of FIGS. 12A, 12B and 12C.

DETAILED DESCRIPTION OF THE INVENTION

Figure 1:
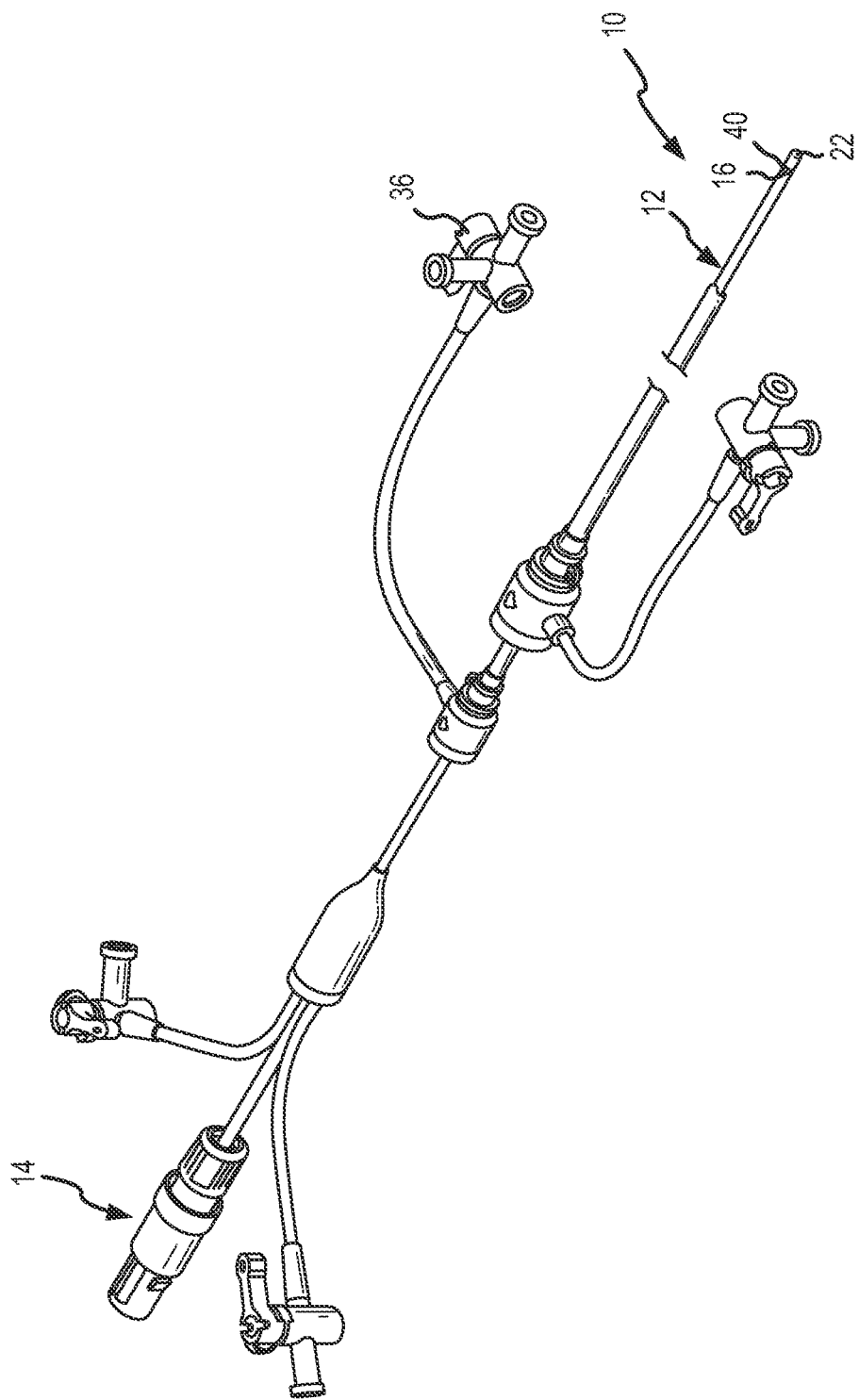
FIG. 1 is one embodiment of an ablation catheter in accordance with the present disclosure.

The ablation catheter 10 of the present invention as shown in FIG. 1 is comprised of a catheter body 12 with a proximal end 14 and a distal end 16, at least one lumen (not shown) extending lengthwise substantially through the catheter body 12, and an electrode (22), secured relative to the distal end 16 of catheter body. In the present embodiment, a heat sink element 40 is disposed between the distal end 16 of the catheter body 12 and the electrode, as will be more fully discussed herein. The catheter body 12 may be a conventional elongated catheter made of materials suitable for use in humans, such as nonconductive polymers. Exemplary polymers used for the production of the catheter body include those well known in the art such as thermoplastic polyurethanes, thermoplastic elastomers (polyamide-based, polyester-based, olefinic and styrenic), polyolefins, nylons, polytetrafluoroethylene, polyvinylidene fluoride, and fluorinated ethylene propylene polymers and other conventional materials.

The length of the catheter 10 may be of any appropriate length typically being between about 50 cm to about 150 cm (20 to 60 in.). The diameter of the catheter 10 is within ranges well known in the industry, generally, from about 4 to 16 French and more preferably from about 6 to 8 French (1 French equals ⅓ of a millimeter (0.013 in.)).

The catheter body 12 generally contains one or more lumens extending through the catheter body 12 from its proximal end to near its distal end. Typically, a sufficient number of lumens are present in the catheter body 12 to accommodate power and control wires for the electrode 22. Lumens may also accommodate, without limitation, wires for thermo sensing devices, such as thermocouples, sensing electrodes and/or electrodes used to gage contact with conductive media or tissue. In addition, in the present embodiment, a fluid irrigation lumen 36 is provided that may be attached to a fluid source to provide, for example, saline through the catheter body 12 to the electrode 22. In one embodiment, such lumens may have a diameter of at least about 0.2 mm (0.008 in.) and more typically from about 0.3 mm (0.01 in.) to about 1.0 mm (0.04 in.).

FIGS. 2A and 2B illustrate electrical current density and thermal conductivity, respectively, of an ablation electrode 22 of an ablation catheter 10 where the ablation electrode 22 (which may be formed of platinum and/or iridium) is attached to the distal end 16 of a catheter body 12. In this regard, the electrically conductive electrode 22 is attached to the substantially insulative (i.e., electrically insulative) distal end 16 of the typically plastic catheter body 12 and is utilized to create a lesion 8 in patient tissue. FIG. 2A illustrates the electrical current density as represented by arrows 26 (i.e., current 26). As will be appreciated, such current density results in Joule heating (i.e., increase in temperature of a conductor as a result of resistance to an electrical current flowing through the conductor) within the electrode 22. Such current density and resulting Joule heating is highest at the interface of the electrode 22 and catheter body 12 due to the large difference of electrical resistivity between the highly conductive electrode 22 and the low conductivity catheter body 12.

Furthermore, the distal end of the plastic catheter body 12 has a low coefficient of thermal conductivity and therefore allow little thermal conduction, as represented by the thick arrows which define heat flow paths 28, from the proximal end of the electrode 22 to the catheter body 12. See FIG. 2B. Accordingly, heat generated within the electrode 22 near the interface may build up over time and create a "hot spot" 30 around the electrode/catheter body interface. This hot spot 30 may have a temperature that is considerably higher than surrounding regions and may heat surrounding blood, which may lead to coagulation.

The heat build up at the electrode/catheter body interface is due in part to the lack of a heat transfer path that is sufficient to transfer heat out of the electrode 22 at a rate which heat is generated within the electrode 22. In this regard, it is noted that the proximal end of the electrode 22 that interfaces with the catheter body 12 depends primarily upon convective heat transfer (e.g., with surrounding blood) to remove heat. Further, depending on the location of the heart chamber and the catheter orientation, blood flow around the proximal end of the electrode 22 may be limited further reducing the effectiveness of the convective heat transfer at the proximal end of the electrode 22. For instance, when an electrode is disposed under the tricuspid valve or mitral valve, there may be little or no blood flow such that there is little convective heat transfer. Accordingly, the electrode/catheter body interface can reach a temperature that causes a hot spot in the surrounding blood, blood coagulation and/or catheter damage.

In contrast, the distal tip of the electrode 22 is in thermal and electrical conduct with myocardium tissue that provides a conductive heat transfer path that allows for increased heat dissipation from the tip of the electrode 22 (i.e., in relation to the proximal end of the electrode 22). That is, due to the contact with the tissue, heat may be conductively transferred from the tip of the electrode 22 thereby preventing or reducing heat build up within the tip of the electrode 22. Accordingly, the tip of the electrode may not reach coagulation temperatures or may take longer to reach coagulation temperatures.

Figure 3B:
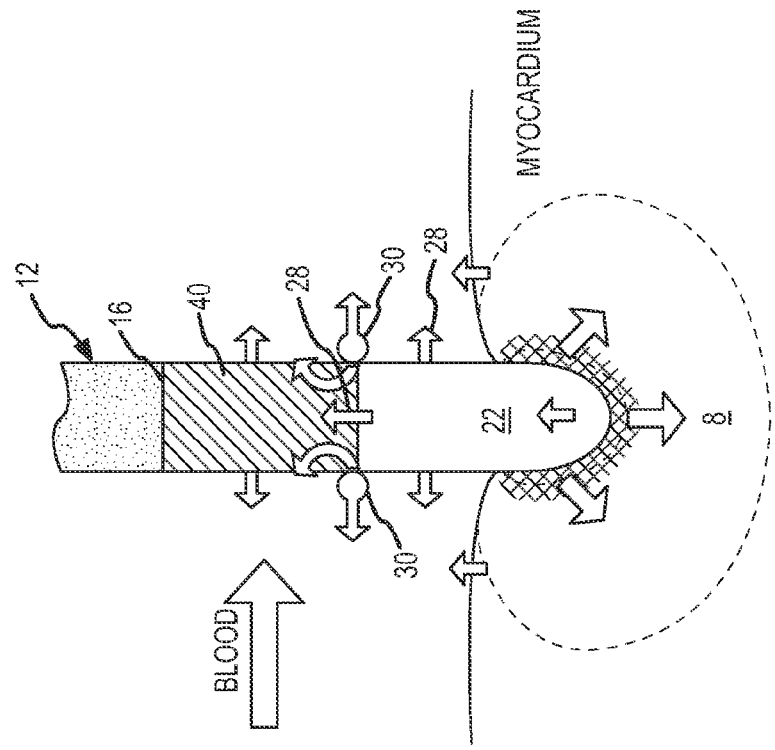
FIGS. 3A and 3B illustrate energy dissipation and thermal conductivity, respectively, in a first embodiment of an ablation electrode in accordance with the present disclosure.
Figure 3A:
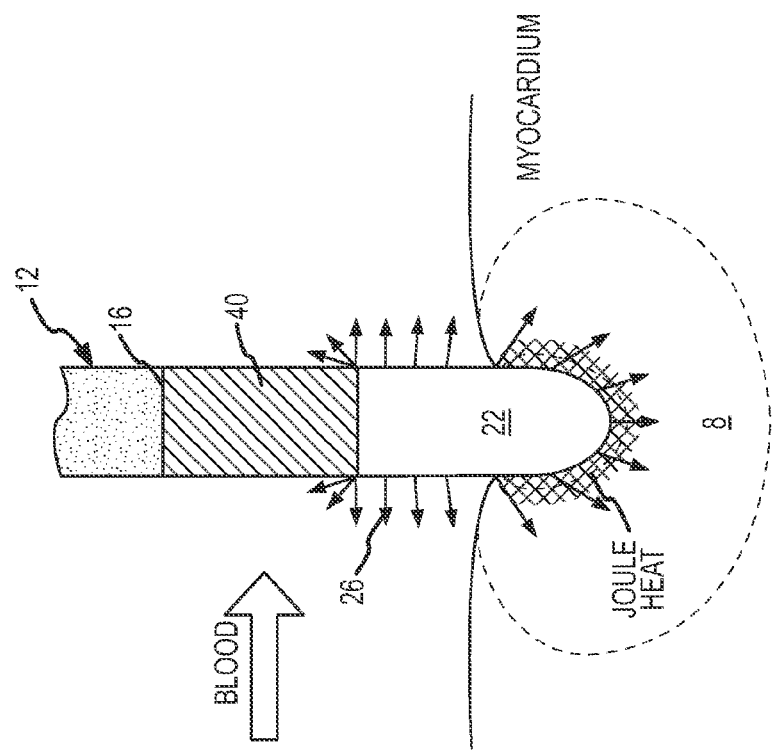

To reduce or substantially eliminate the temperature build up at the interface between the electrically conductive electrode 22 and the electrically and thermally insulative catheter body 12, the electrode embodiment of FIGS. 3A and 3B disposes a heat sink 40 between the electrode 22 and the distal end 16 of the catheter body 12. This heat sink 40 is an electrically insulative (e.g., an electrical isolator) but thermally conductive element. As it is electrically insulative, the electrical field within the electrode 22 as shown in FIG. 3A behaves substantially the same as the electrical field within the ablation electrode as shown in FIG. 2A. In this regard, little or no current 26 flows into the electrically insulative heat sink 40. Accordingly, there is little or no joule heating in the heat sink 40. However, as the heat sink 40 is thermally conductive, heat is extracted from the proximal end of the electrode 22 thereby reducing and/or preventing heat build up in the electrode 22. This reduces or prevents the generation of a hot spot 30 in the surrounding blood. That is, heat is conducted away from the proximal end of the electrode 22 and distributed throughout the heat sink 40, which provides additional surface area for dissipating the heat. That is, the combined surface area of the heat sink 40 and electrode 22 allows for more readily dissipating heat from the electrode 22 to reduce or prevent heat build up and/or the generation of a hot spot 30. That is, the combined surface area improves convective heat transfer from the proximal end of the electrode. Further, the heat sink may absorb heat from surrounding blood to help avoid coagulation.

In addition to reducing the temperature of the proximal end of the electrode 22, the heat sink 40 may also reduce the overall temperature of the electrode 22. It will be appreciated that for single location ablation procedures, energy may be applied to the electrode 22 for short durations. Accordingly, contact with the tissue and the short duration of applied energy typically prevents heat build up in the tip of the electrode 22. However, in other ablation procedures such as drag burn procedures, energy may be applied to the electrode 22 for longer durations. These longer duration procedures may result in heat build up throughout the entire electrode 22 including the portion of the electrode in contact with tissue. Such heat build up can result in coagulation of surrounding blood as well as tissue charring (e.g., myocardium charring). Accordingly, use of the heat sink 40 may allow for reducing the overall temperature of the electrode 22 including the temperature at the electrode/tissue interface. This can reduce or prevent coagulation and/or tissue charring. However, it will be noted that this electrode temperature reduction (i.e., electrode cooling) only affects the electrode tissue interface and does not adversely affect the thermal conduction inside the tissue. In this regard, temperatures within the tissue may be increased to a desired temperature to create a lesion 8 having a desired depth.

It will be appreciated that any suitable electrically insulative and thermally conductive material may be utilized as a heat sink. As shown, Table 1 illustrates a non-limiting group of materials that may be utilized as an electrically insulative heat sink. Specifically, Table 1 shows the resistivity and thermal conductivity of various materials. Also included in Table 1 for purposes of comparison are the resistivity and thermal conductivity of tissue, blood, polyurethane (e.g., a non-conductive catheter body), and a platinum/iridium electrode.

TABLE 1

|  | ρ (Ω · cm) | k(W/cm · K) |
|---|---|---|
| Tissue | 200 | 0.0055 |
| Blood | 150 | 0.0055 |
| Electrode (Pt/Ir) | $2.5 \cdot 10^{-5}$ | 0.7 |
| Polyurethane | $>10^7$ | 0.00026 |
| Diamond/Diamond-like Carbon | $>10^7$ | 20 |
| Aluminum Nitride | $10^7$ | 3.7 |
| Boron Nitride | $>10^7$ | 13 (theory) |
| CoolPoly | $>10^7$ | 0.1 |
| Silicone | 0.0025 | 1.5 |
| Thermal Epoxy | $>10^7$ | 0.01 |

As shown, materials suitable for use as an electrically insulative and thermally conductive heat sink include diamond/cubic zirconium, diamond-like carbon, ceramics, such as aluminum nitride, boron nitride, silicon carbide and alumina. Each of these materials provides electrical resistivity in conjunction with thermal conductivity. That is, these materials typically exhibit resistivity that is several orders of magnitude greater than tissue or blood while also having a thermal conductivity that is at least an order of magnitude greater than tissue or blood.

FIGS. 3A, 3B and 4-7B illustrate various configurations of a distal end 16 of an ablation catheter including an electrode 22 and an electrically insulative thermal heat sink 40. As shown in FIG. 3A, the heat sink 40 may be formed as a substantially solid piece that is attached to the proximal portion of the electrode 22 and to the distal end 16 of the catheter body 12. In this regard, the electrode 22 and heat sink 40 may be disposed in series. In such an arrangement, the outside surfaces of these components 22, 40 may be conformal (e.g., cylindrical) and/or may match the outside surface of the catheter body 12. As will be appreciated, in such an arrangement the solid heat sink 40 may include an internal passageway/lumen to allow for electrical and or fluid connections between the electrode and the distal end of the catheter body 12. Further, such a lumen may allow for a guide wire to extend through the heat sink 40 to the electrode 22.

Figure 4A:
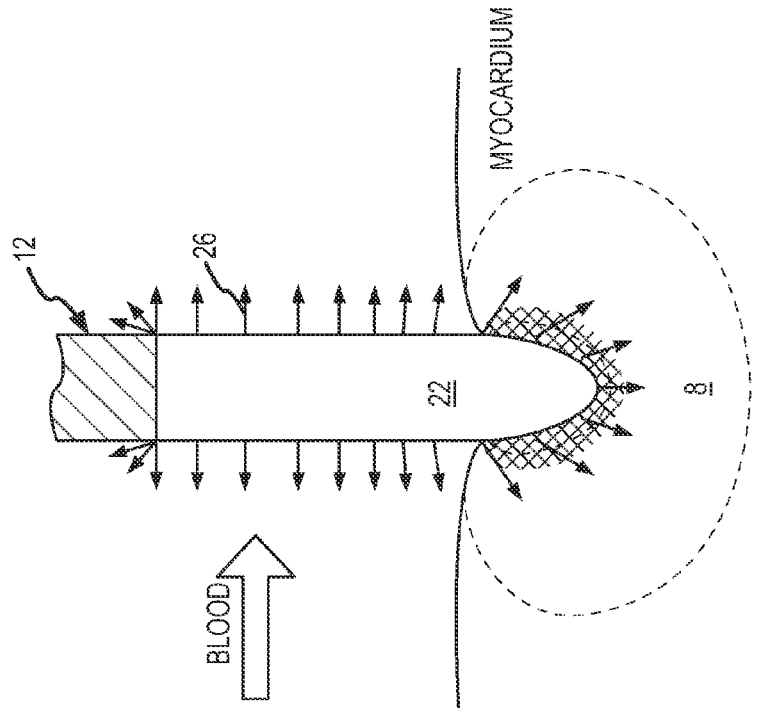
FIGS. 4A and 4B illustrate energy dissipation and thermal conductivity, respectively, in a second embodiment of an ablation electrode in accordance with the present disclosure.
Figure 4B:
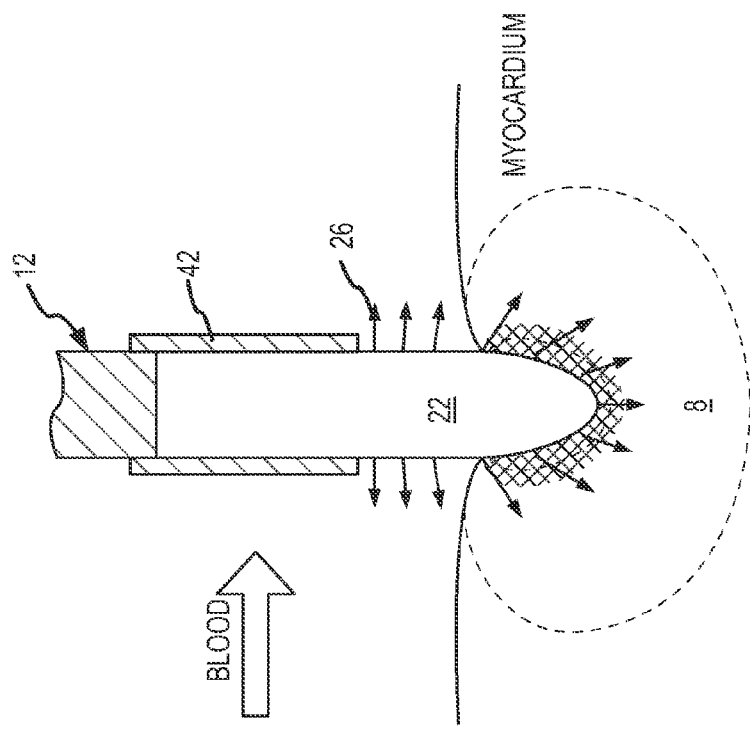

In another arrangement, shown in FIG. 4A, an electrically insulative heat sink is formed as a coating or casing 42 that is dispose about an outside portion of the electrode 22 and/or catheter body 12. Such a casing 42 may be applied as a tape or film or as a rigid cylinder applied to an outside surface of the electrode 22 and/or catheter body 12. It will be noted that such a casing or coating may be applied to existing electrodes to improve their functional qualities. For instance, larger/longer electrodes have previously been utilized to increase the convective area of the electrode and thereby reduce the temperature of the electrode. For instance, FIGS. 4A and 4B illustrates an 8 mm electrode whereas FIGS. 3A and 3B illustrates a 4 mm electrode. The larger electrode of FIGS. 4A and 4B provides a larger conductive surface area that allows for reducing the temperature of the electrode during operation. However, the larger conductive surface area results in dissipation of ablation power into the surrounding fluid (e.g., saline or blood). See FIG. 4B. Accordingly, such larger/longer electrodes have required increased ablation power.

By providing an electrically insulative casing or coating 42 about a proximal portion of the electrode 22 (See FIG. 4A), energy dissipation from the proximal portion of the electrode may be reduced or substantially eliminated. Of note, embodiments where an electrically insulative casing or coating is applied to a proximal portion of an electrode, the casing or coating need not have a high coefficient of thermal conductivity as long as the casing or coating is thin enough such that heat can easily dissipate through the casing/coating. In one arrangement, a heat shrink tape or tube may be applied around a proximal portion of an electrode. Such a heat shrink tape is typically thin enough to allow for ready transfer of heat while electrically substantially isolating a proximal portion of the electrode.

FIGS. 5A and 5B illustrate a third embodiment of an electrode having a thermally conductive heat sink. In the embodiment of FIGS. 5A and 5B, the distal end 16 of the catheter body 12 forms a heat sink. In this regard, all or at least the distal portion 16, of the catheter body 12 is formed of thermally conductive compound. For instance, a thermally conductive polymer or plastic such as Coolpoly® from Cool Polymers, Inc. of 333 Strawberry Field Rd. Warwick, R.I. 02886, may be utilized. In such an arrangement, the thermally conductive catheter body 12 may provide insulation of electrical current 26 between the electrode 22 and the catheter body 12 (See FIG. 5A) to prevent diversion of ablation energy while also providing a thermal conduction or heat flow path 28 (See FIG. 5B) to dissipate heat generated within the electrode 22. Again, such thermal conduction may prevent heat build-up in the electrode 22 and/or reduce or prevent the generation of a hot spot 30 in surrounding fluid.

FIGS. 6A, 6B and 6C illustrate another embodiment of an ablation electrode 22 incorporating an electrically insulative thermal heat sink 40. As shown, the heat sink 40 is disposed in parallel with the electrode 22. More specifically, in this particular embodiment both the electrode 22 and heat sink 40 form a half-cylinders that are interconnected along their axial length. In such an arrangement, the electrode 22 may be placed in contact with patient tissue (e.g., myocardium) in order to focus energy (i.e., current 26) into the tissue to create a lesion 8. See FIG. 6B. In such an arrangement, the heat sink 40 is exposed to blood for thermal convection. Again, the heat sink 40 provides a heat flow path 28 for removing heat from the electrode 22. According, thermal conduction into the heat sink reduces temperature over the length of the ablation electrode. In such an arrangement, the overall length of the electrode may be sufficient to create linear lesions, for example, for AFL or AFIB ablation procedures.

FIGS. 7A and 7B illustrate another embodiment of an ablation electrode that utilizes an electrically insulative and thermally conductive heat sink 40. As shown, the ablation electrode 22 is again attached the distal end 16 of a catheter body 12 and a thermally conductive and electrically insulative heat sink 40 is disposed between the electrode 22 and the catheter body 12. Additionally, the catheter body 12, heat sink 40 and electrode 22 each include common internal passageways 44. These passageways 44 are adapted to carry a liquid coolant (e.g., saline) from the proximal end of the catheter through the distal tip of the electrode 22. In this regard, tissue contacted by electrode 22 may be bathed in coolant/saline during an ablation procedure. As will be appreciated, use liquid coolant passing through the electrode 22 may help control the temperature of the electrode 22.

Further, as shown in the cross-sectional view of FIG. 7B, it may be desirable to electrically insulate or isolate the coolant passageway 44 from the electrode 22. In this regard, a thermally conductive and electrically insulative barrier 46 (e.g., tube or cylinder) may be utilized to line the passageway 44. Such a barrier 46 may electrically isolate the passageway 44 from the electrode and or a conductive coil 48 that provides electrical energy to the electrode 22, while still permitting heat exchange between coolant passing through the passageway 44 and electrode 22. In this regard, coolant passing through the passageway 44 may provide cooling for the electrode 22 without dissipating energy from the electrode 22.

FIGS. 8-11 graphically illustrate lesion depth, power, catheter temperature, and differences between the electrode of FIGS. 3A and 3B incorporating the heat sink 40, the larger electrode of FIG. 4A incorporating an electrically insulative casing/coating 42 and the larger electrode of FIG. 4B without a casing/coating or heat sink. Respectively, these electrodes are referred to as a 4 mm electrode, a 8 mm coated electrode and a 8 mm standard electrode. It will be appreciated that these sizes are presented by way of example and not of limitation of the present disclosure.

Figure 8:
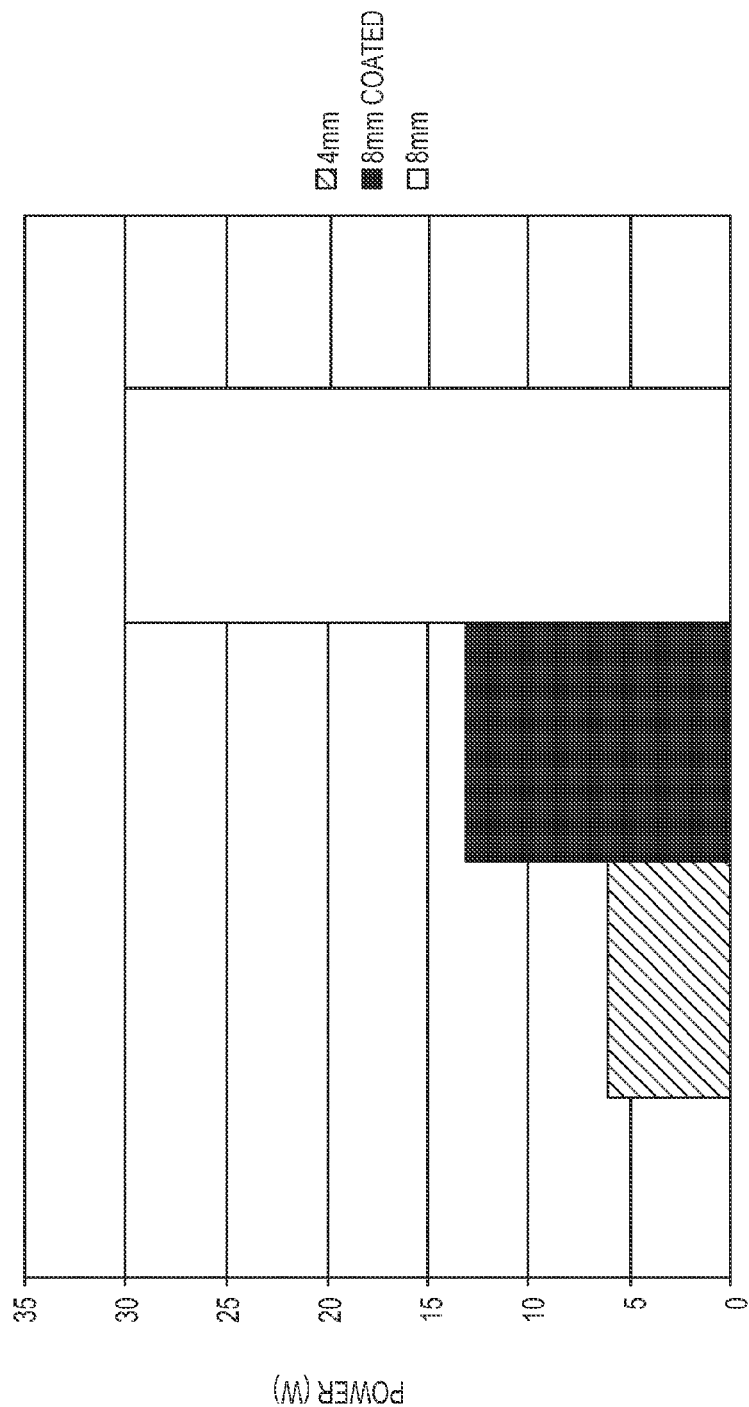
FIG. 8 is a graph illustrating power of different electrode configurations under temperature controlled ablation.

FIG. 8 illustrates the power required by each of the electrodes to maintain a 75 degree Celsius temperature. As shown, the 4 mm electrode requires the least power. Of particular note, the 8 mm coated electrode requires less than one-half the power of the 8 mm standard electrode. That is, the casing/coating 42 significantly reduces or eliminates the energy dissipation from the coated portion of the electrode. Accordingly, as less power is dissipated into the surrounding fluid, more energy may be available to form a lesion within the tissue.

Figure 9:
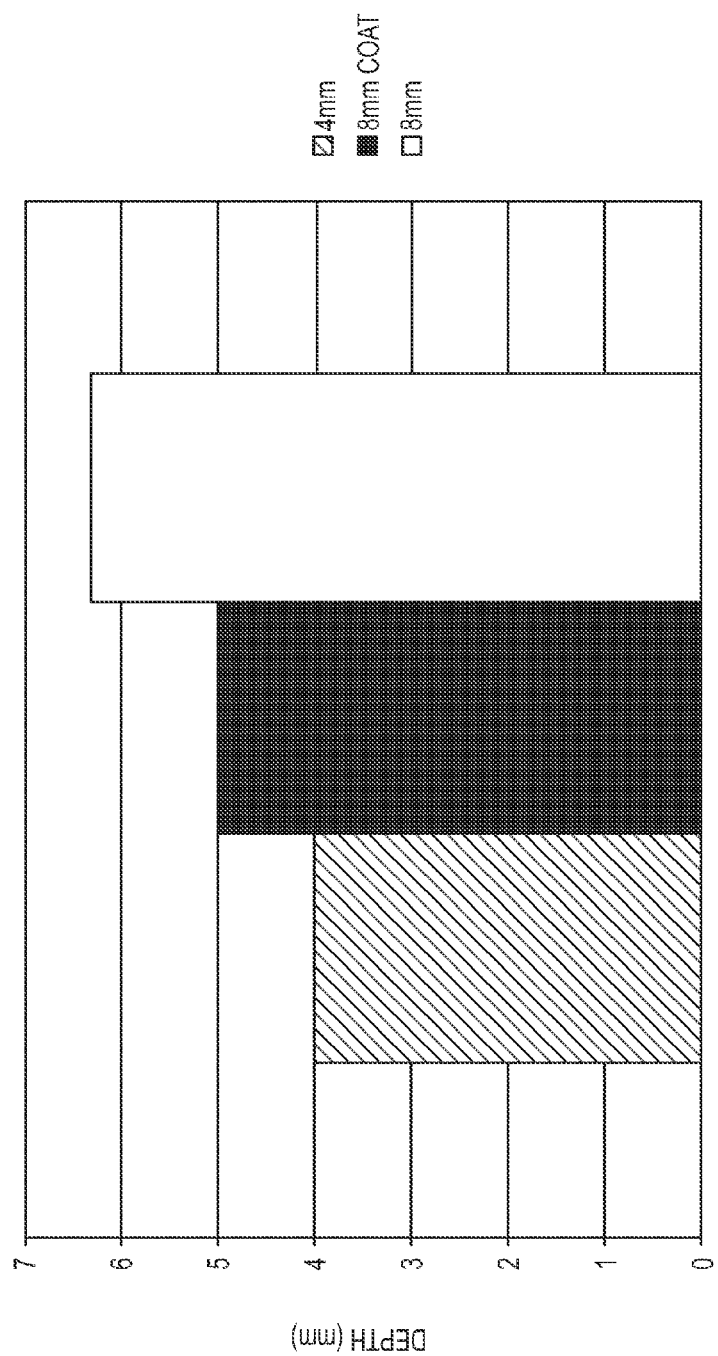
FIG. 9 is a graph illustrating lesion depths for the different electrode configurations of FIG. 8.

FIG. 9 illustrates the lesion depth of the 4 mm electrode, the 8 mm coated electrode and 8 mm standard electrode. As shown, the 8 mm standard electrode produces the deepest lesion. Specifically, the 8 mm uncoated electrode lesion is approximately 15% deeper than the lesion created by the 8 mm coated electrode. However, it will be appreciated that the deeper lesion was produced using approximately twice the power of the 8 mm coated electrode. Accordingly, if a 8 mm coated electrode is utilized, such additional power would be available to create a deeper lesion. This is also true for the 4 mm electrode incorporating the heat sink.

Figure 10:
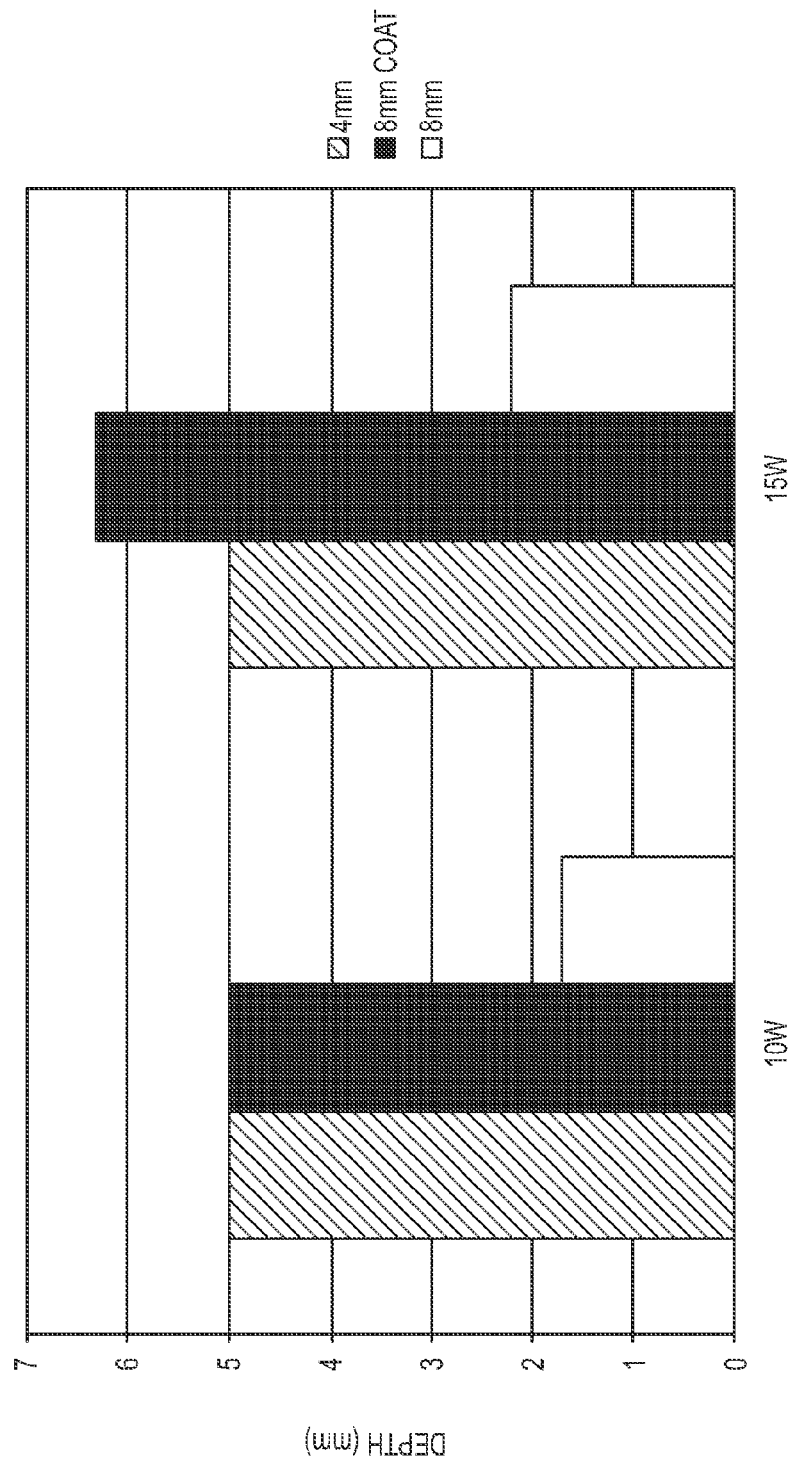
FIG. 10 is a graph illustrating lesion depth of different electrode configurations under power controlled ablation.
Figure 11:
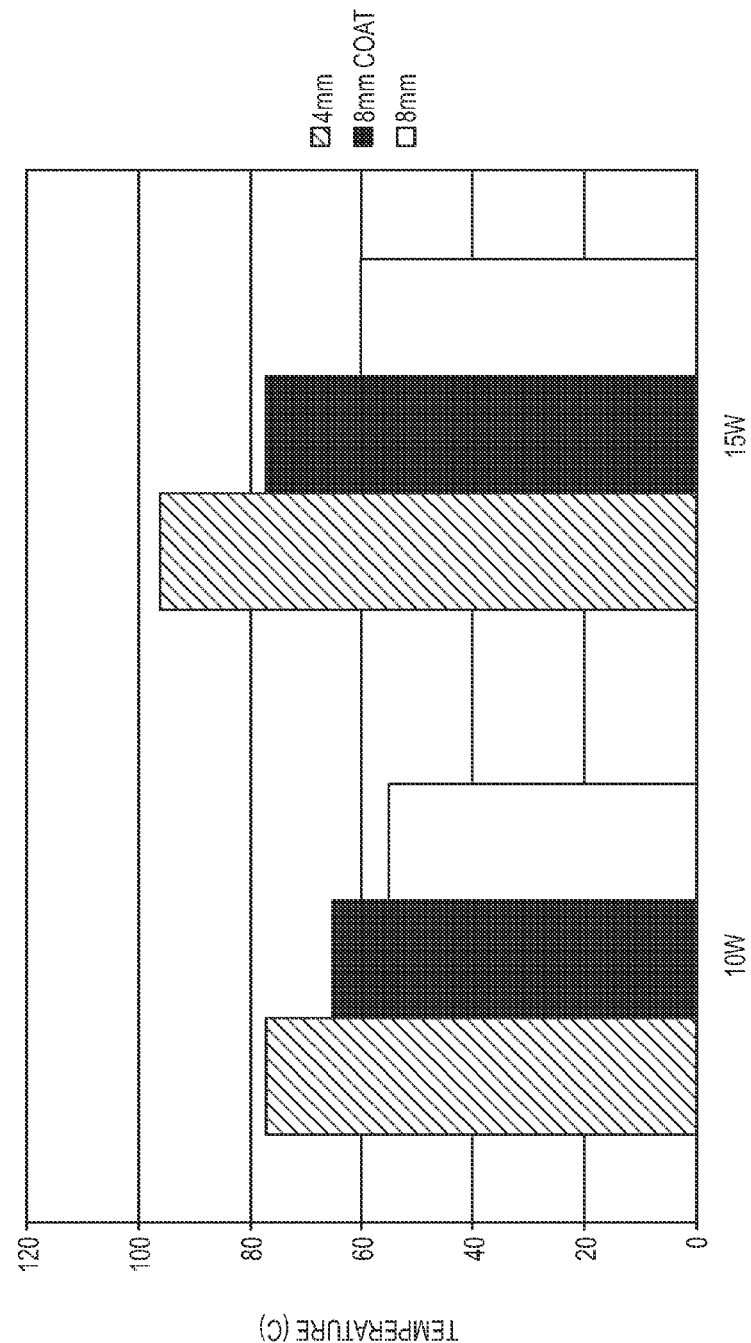
FIG. 11 is a graph illustrating temperatures for different electrode configurations for the power controlled ablation of FIG. 10.

FIGS. 10 and 11 illustrate catheter temperature and lesion depth under controlled power ablation. That is, in response to a fixed power level being applied to the electrode, the depth of the lesion is measured and the corresponding temperature of the electrode is measured. As shown in FIG. 10, the depth of the lesion created by an applied power of 10 watts is substantially the same for the 4 mm electrode of FIG. 3A and the 8 mm coated electrode of FIG. 4A. The depth of the lesion is slightly greater for the 8 mm coated electrode for an applied power of 15 watts. In either case, the depth of the lesion of the 4 mm electrode using the heat sink and the 8 mm coated electrode is significantly greater than that of the 8 mm standard electrode. For instance, lesion depths of the 4 mm electrode using a heat sink and 8 mm coated electrode are between about two and three times deeper than the lesion depth of the 8 mm standard electrode. This is due in part to the reduced dissipation of energy into surrounding media (e.g., blood). That is, the standard electrode dissipates energy into surrounding fluid that may otherwise be utilized to generate a lesion. Use of either an electrode with a heat sink or a coated electrode reduces such energy dissipation.

FIG. 11 illustrates the catheter temperature for the 4 mm, 8 mm coated and 8 mm standard electrode at different power levels. As shown, the 4 mm electrode using the heat sink and the 8 mm coated electrode reach higher temperatures than the 8 mm standard electrode. However, the temperatures of the 4 mm electrode using the heat sink and the 8 mm coated electrode may be maintained within acceptable limits while providing significant improvements in lesion depth as noted in relation to FIG. 10.

Figure 12A:
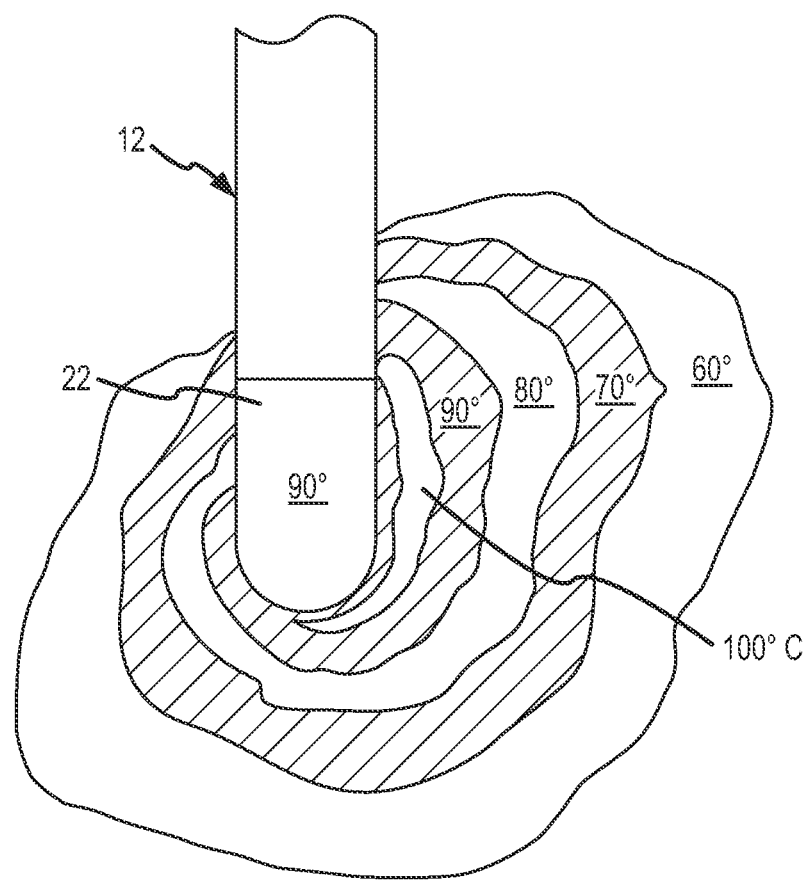
FIGS. 12A, 12B and 12C are graphs of temperature distribution in tissue for different electrode configurations.
Figure 12B:
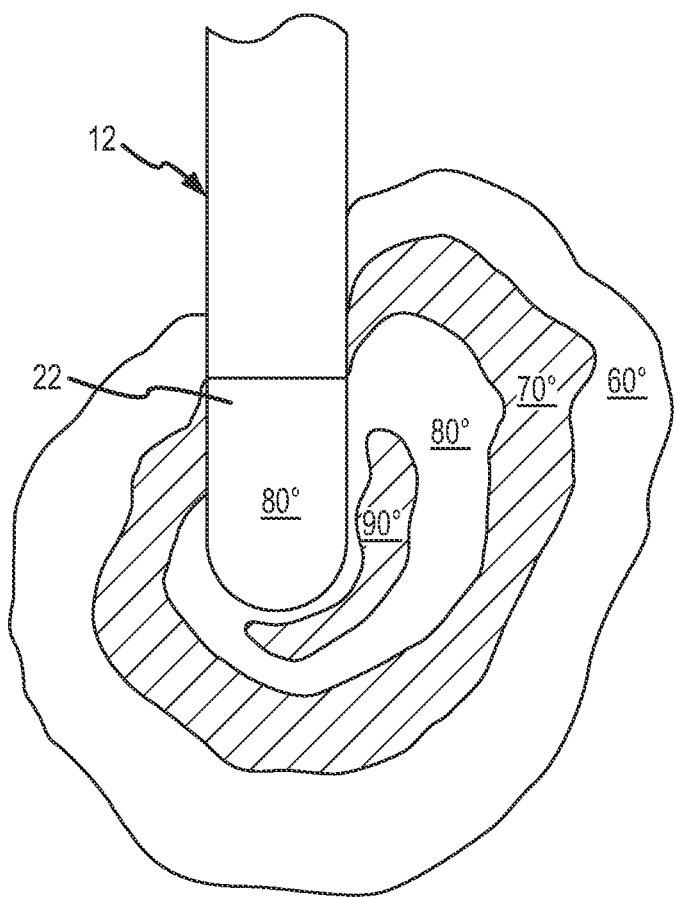
Figure 12C:
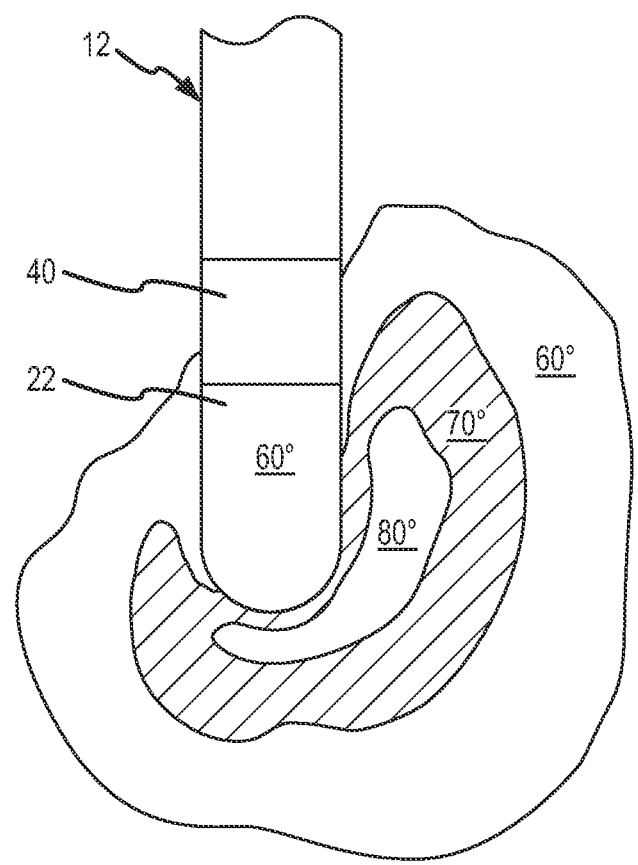

FIGS. 12A, 12B and 12C illustrate temperature distribution within patient tissue contacted by an electrode 22 under identical operating conditions. Specifically, FIG. 12A illustrates the temperature distribution of an electrode 22 and surrounding tissue for an electrode without a heat sink (e.g., as shown in FIG. 2A) where the proximal end of the electrode 22 contacts a thermally and electrically insulative plastic catheter body 12. FIG. 12B illustrates the temperature distribution of an electrode and surrounding tissue for an electrode that utilizes a thermally conductive catheter body 12 (e.g., a thermal polymer embodiment as shown in FIG. 5A). FIG. 12C illustrates temperature distribution of an electrode and surrounding tissue for an electrode that utilizes a heat sink connected to its proximal end (e.g., as shown in FIG. 2A).

Results of the three temperature distributions are tabulated in FIG. 13. As illustrated, the electrode or 'plastic' embodiment of FIG. 12A results in a maximum tissue temperature of approximately 95 degrees Celsius, a maximum electrode temperature of approximately 85 degrees Celsius and a 5.2 mm lesion depth. In contrast, the thermal polymer embodiment of 12B results in a maximum temperature of approximately 84 degrees Celsius of the tissue, a maximum electrode temperature of approximately 70 degrees Celsius and a 5 mm lesion depth. Finally, the embodiment of 12C utilizing the heat sink, which in this embodiment comprises an aluminum nitrate heat sink, results in a maximum tissue temperature of approximately 74 degrees Celsius, a maximum electrode temperature of approximately 56 degrees Celsius and a lesion depth of 4.9 mm. As shown, use of a thermally conductive catheter or a heat sink significantly reduces the tissue temperature and electrode temperature while minimally affecting the lesion depth. As will be appreciated, this may prevent or eliminate tissue charring during ablation procedures.

In addition to reducing the likelihood of tissue charring, it will be appreciated that the lowered electrode and tissue temperatures may allows for the provision of additional power to the electrode. Such additional power may be utilized to create lesions having increased depth without increasing electrode and/or tissue temperatures beyond desired thresholds.

Although five embodiments of this invention have been described above with a certain degree of particularity, those skilled in the art could make numerous alterations to the disclosed embodiments without departing from the spirit or scope of this invention. For example, it will be appreciated that a catheter may include multiple electrodes and/or multiple heat sinks. Further, it will be recognized that all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ablation catheter, comprising:
a catheter body, the catheter body comprising a proximal portion and a distal end, the distal end being adapted to be inserted into a body cavity;
an ablation electrode connected relative to the distal end of the catheter body; and
a thermally conductive and electrically resistive heat sink in thermal contact with the ablation electrode, and being electrically insulated from the ablation electrode, wherein at least a portion of the heat sink forms a portion of an outside surface of the ablation catheter.

2. The catheter of claim 1, wherein the heat sink has an electrical resistivity of at least $1.0 \times 10^3$ ohm centimeters.

3. The catheter of claim 1, wherein the heat sink has a thermal conductivity of at least 0.01 watts per centimeter Kelvin.

4. The catheter of claim 1, wherein the distal end of the catheter body forms the heat sink.

5. The catheter of claim 4, wherein at least the distal end of the catheter body comprises a thermally conductive polymer.

6. The catheter of claim 1, wherein the heat sink is disposed between the ablation electrode and the distal end of the catheter body, wherein the heat sink physically separates the electrode from the distal end of the catheter body.

7. The catheter of claim 6, wherein the heat sink further comprises:
an internal passageway extending between the ablation electrode and the distal end of the catheter body.

8. The catheter of claim 7, wherein the ablation electrode further comprises:
an internal passageway in communication with the internal passageway of the heat sink, wherein the internal passageways are adapted to receive fluid from the distal end of the catheter body.

9. The catheter of claim 8, wherein the catheter body further comprises:
at least one lumen for providing a fluid flow to the internal passageway of the heat sink.

10. The catheter of claim 6, wherein the ablation electrode and the heat sink have a common cross-sectional profile.

11. The catheter of claim 1, wherein the electrode extends between a proximal end and a distal end and wherein the heat sink is in thermal contact with the ablation electrode over a portion of the length of the ablation electrode between the proximal and distal ends.

12. The catheter of claim 11, wherein the heat sink is in thermal contact over substantially the entire length of the ablation electrode.

13. An ablation catheter, comprising:
a catheter body, the catheter body comprising a proximal portion and a distal end, the distal end being adapted to be inserted into a body cavity;
an ablation electrode; and
an electrically insulative and thermally conductive heat sink having a first end connected to the distal end of the catheter body and a second end that is connected to and supports the ablation electrode, wherein said heat sink substantially isolates said ablation electrode from the distal end of the catheter body.

14. The catheter of claim 13, wherein the heat sink has an electrical resistivity of at least $1.0 \times 10^3$ ohm centimeters.

15. The catheter of claim 13, wherein the ablation electrode has a distal tip for contacting tissue and the heat sink is connected to a proximal end of the electrode.

16. The catheter of claim 13, wherein the heat sink has a thermal conductivity of at least 0.05 watts per centimeter Kelvin.

* * * * *